US012740846B1

(12) United States Patent
Whang et al.

(10) Patent No.: US 12,740,846 B1
(45) Date of Patent: Sep. 22, 2026

(54) DYNAMIC ELASTIC SUSPENSION SYSTEM AND FRAME FOR FUNCTIONAL ENDOSCOPIC SINUS SURGERY

(71) Applicants: Joan Whang, Elk Grove, CA (US); Christopher Sung Whang, Modesto, CA (US)

(72) Inventors: Joan Whang, Elk Grove, CA (US); Christopher Sung Whang, Modesto, CA (US)

( * ) Notice: Subject to any disclaimer, the term of this patent is extended or adjusted under 35 U.S.C. 154(b) by 0 days.

(21) Appl. No.: 19/083,682

(22) Filed: Mar. 19, 2025

(51) Int. Cl.
*A61B 1/00* (2006.01)
*A61B 90/50* (2016.01)

(52) U.S. Cl.
CPC .......... *A61B 90/50* (2016.02); *A61B 1/00128* (2013.01); *A61B 2090/5025* (2016.02)

(58) Field of Classification Search
CPC ............ A61B 90/50; A61B 2090/5025; A61B 1/00121; A61B 1/00147; A61B 1/00149; A61B 8/4227; B25H 1/0028
See application file for complete search history.

(56) References Cited

U.S. PATENT DOCUMENTS 3,666,220 A * 5/1972 Rider .................. B23Q 1/0027 267/156
5,059,145 A * 10/1991 Gregg .................. B63H 16/04 114/347
5,367,924 A * 11/1994 Henson ................ B25H 1/0028 81/57.24
5,609,316 A * 3/1997 Tigliev ................ F16M 11/105 248/292.11
6,334,595 B1 * 1/2002 Stenkvist ............ B25H 1/0028 248/176.1
2006/0126167 A1 * 6/2006 Piontkowski .......... F16M 13/02 359/368
2007/0129634 A1 * 6/2007 Hickey ................ F16M 13/027 600/439
2010/0243845 A1 * 9/2010 Lepine .................... B25H 3/00 248/315
2012/0295727 A1 * 11/2012 Smed ................ A63B 21/4035 473/422
2016/0120611 A1 * 5/2016 Lohmeier ............. A61B 90/50 606/130
2018/0333632 A1 * 11/2018 Mitsis-Koutoukis ....................... A63B 21/068
2019/0365211 A1 * 12/2019 Duan .................... A61B 1/041
2021/0268327 A1 * 9/2021 Kushner ............. A63B 21/018
2023/0329816 A1 * 10/2023 Kumar .............. A61B 1/00042
2024/0210310 A1 * 6/2024 Cutrale ............... A61B 1/0623

* cited by examiner

*Primary Examiner* — Anhtuan T Nguyen
*Assistant Examiner* — Rynae E Boler
(74) *Attorney, Agent, or Firm* — Adam Warwick Bell; Matthew Rupert Kaser

(57) ABSTRACT

An elastic suspension system and frame for supporting an endoscope and camera combination used in functional endoscopic sinus surgery. the system consists of a stable base, an adjustable frame, and an elastic suspension mechanism that dynamically counterbalances the weight of the endoscope and camera, significantly reducing surgeon fatigue and improving precision. The invention includes variations incorporating powered gimbal stabilization and spring-based equilibrium mechanisms to enhance functionality and adaptability across surgical applications.

4 Claims, 3 Drawing Sheets

DYNAMIC ELASTIC SUSPENSION SYSTEM AND FRAME FOR FUNCTIONAL ENDOSCOPIC SINUS SURGERY

GOVERNMENT SUPPORT

None

FIELD OF THE INVENTION

The present invention relates to surgical equipment, and more particularly, to a dynamic elastic suspension system and frame designed to support an endoscope and camera combination used in Functional Endoscopic Sinus Surgery (FESS), thereby reducing hand fatigue and improving surgical precision.

BACKGROUND OF THE INVENTION

Endoscopic sinus surgery is a delicate medical procedure requiring precision and steady hand control.

Performing Endoscopic sinus surgery using an endoscope inherently has a number of practical problems. These include Fogging and Obstruction—The lens can become foggy due to temperature differences or get covered in blood and mucus, requiring frequent cleaning and disrupting the procedure. Instrument Clashing—In functional endoscopic sinus surgery (FESS), the surgeon must operate through small nasal passages using multiple instruments. Manoeuvring the endoscope while also using other tools can lead to hand fatigue and instrument crowding. Stability Issues—Holding and adjusting the endoscope manually can cause unwanted camera movement, leading to instability in the view.

Although this is a long felt need, there has never been a suitable device to address it. Relevant devices and inventions include "Surgical System Instrument Manipulator" (EP2568909A1). This patent describes an instrument manipulator within a robotic surgical system, designed to control surgical instruments with precision. The manipulator focuses on robotic control mechanisms rather than an elastic suspension system. It lacks components like an elastic suspension element or a counterbalancing mechanism to support the weight of the instrument dynamically. Another interesting reference is the "Belleville Spring Elastic Suspension" (U.S. Pat. No. 3,107,905A) that discloses a Belleville spring elastic suspension system designed for isolating a mass with a given weight. Although it involves an elastic suspension mechanism, it is not tailored for medical instruments or surgical use. The design does not consider the specific needs of supporting surgical instruments, such as endoscopes, during procedures.

Traditionally, surgeons must hold an endoscope and camera combination in one hand throughout the procedure, leading to arm fatigue, hand tremors, and reduced accuracy over time. Existing solutions, such as rigid metal holders, fail to provide dynamic movement, making them unsuitable for this application. There is a need for an apparatus that can support the weight of the endoscope while allowing free movement necessary for effective surgical performance.

SUMMARY OF THE INVENTION

The present invention provides a novel elasticated suspension system and frame, designed to support and dynamically suspend an endoscope and camera combination. The system generally consists of:

(i) A stable base for structural support.

(ii) An adjustable metal frame connected to the base to accommodate different heights.

(iii) An elasticated suspension element that attaches between the frame and the endoscope/camera assembly, effectively counterbalancing the weight and reducing strain on the surgeon's hand and arm.

The elasticity of the suspension system enables continuous, smooth movement of the endoscope and camera, crucial for effective endoscopic sinus surgery. This invention enhances surgeon comfort, reduces fatigue, and increases precision, addressing the shortcomings of the current standard approach.

DETAILED DESCRIPTION OF THE INVENTION

Figure 1:
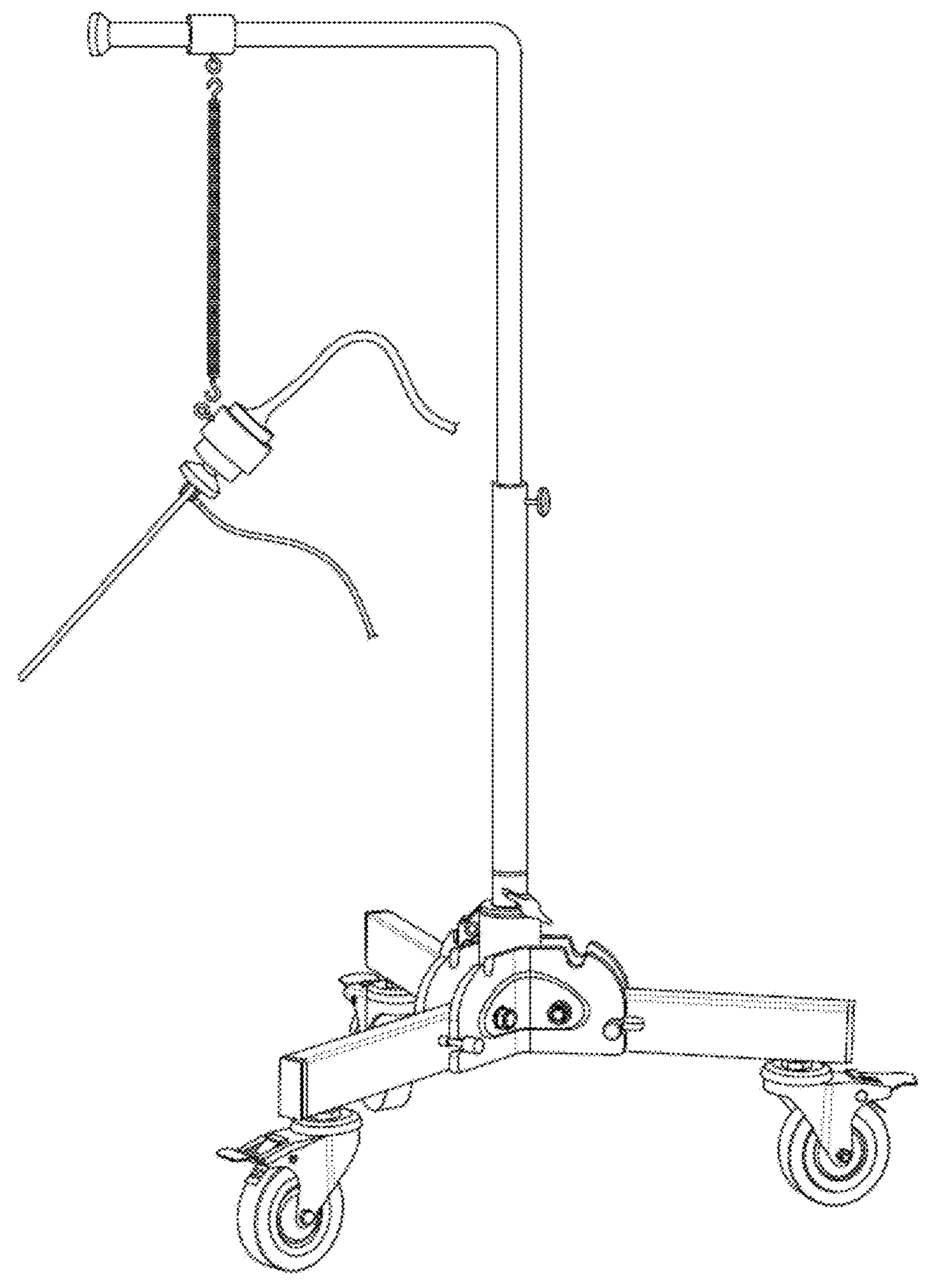
FIG. 1: Perspective view of the elasticated suspension system and frame of the invention.

The device of the invention encompasses an elasticated suspension system that comprises a frame (sometimes called a gantry) and an elasticated suspension element adapted to support an endoscope. The system is adapted to dynamically suspend an endoscope and camera combination such that the endoscope is supported and "floats" in such a way that it can be moved and manipulated by the surgeon, accurately and with minimal muscular effort, and does not have to be constantly held in place.

Currently ENT surgeons hold the endoscope/camera combination in one hand during Endoscopic Sinus Surgery which creates significant arm and hand fatigue, leading to tremor, loss of precision and discomfort during these types of surgeries. There is currently no device that will support the weight of the endoscope and camera combination and simultaneously allow dynamic movement of the endoscope/camera which is critical during endoscopic sinus surgery.

Although the examples of the present invention describes a an elasticated suspension system for supporting an endoscope use in sinus surgery, it is equally applicable to any endoscope, such as those use for oesophageal, gastroscopic and other internal imaging uses.

The weight of an average endoscope depends on its type and purpose. However, a standard flexible endoscope (like a gastroscope or colonoscope) typically weighs between 1.5 to 3.5 pounds (0.7 to 1.6 kg). Rigid endoscopes, used for procedures like arthroscopy or laparoscopy, are usually lighter, often around 0.5 to 2 pounds (0.2 to 0.9 kg) since they have a simpler structure. An endoscope used for sinus surgery (a rigid nasal endoscope) typically weighs between 200 to 400 grams (0.44 to 0.88 pounds). The exact weight depends on the diameter (usually 2.7 mm or 4 mm) and length (typically 18-30 cm) of the scope.

These endoscopes are designed to be lightweight for easy maneuverability during Functional Endoscopic Sinus Surgery (FESS) and related procedures.

The device comprises an elasticated suspension system that comprises a frame and an elasticated suspension element attached to the frame (or integrated into the frame), adapted to support an endoscope.

The frame may be adapted to stand on the floor. It may have a weighted base, or a base secured to the floor with fastenings, such as bolts or screws or glue. Or the base may have plastic or rubber (or similar) feet to stop it from slipping once in place. Or the base may be moveable, for example using wheels or sliders affixed to the base. In this case the base will also include a breaking mechanism for securing the base in place without moving once it is suitably positioned for use. In another embodiment the base may be moveable with the use of rails, wherein the rails are fixable to the floor, allowing the base to move backwards and forwards along the fixed rails.

The frame will comprise a base and an upright beam (upright member) securely attached to the base. The upright beam will have a lower end and an upper end and extend generally vertically from the base.

The upright beam may have attached thereto a lateral support beam, attached laterally to the upper end of the upright beam.

The upright beam may itself serve as a sprung element of the device and be fashioned as a curved member (or straight but curvable member when force is applied) curving up and outward from the base to provide a flexible and sprung support from which the endoscope may be secured via an elongated flexible tie such as a wire or chain or rope.

The elongated flexible tie may be functionally elasticated or not elasticated or partially elasticated. The elongated flexible tie may be made of a single elasticated portion, such as a polymer (synthetic rubber) tube, metal spring, band or rope as commonly used in "exercise bands", or may have one portion of its length composed of an elasticated portion, and one or two other portions composed of a non-elasticated substance.

The lateral support beam, if there is one, will extend a certain desired distance away from the centre of gravity of the upright member and may be straight, curved or cantilevered. The lateral support beam may be ridged of flexible. It will have a proximal end, generally fixed to the upright member, and a distal end, further away from the upright member adapted to attach, at the far distal end, an elongated flexible tie to which is attached, and from which is suspended, the endoscope. The lateral support beam, may itself serve as the elasticated or flexible element of the device and be fashioned as a curved member or straight but curvable member when force is applied to provide a flexible and sprung support from which the endoscope may be secured via an elongated flexible tie such as a wire or chain or rope.

EMBODIMENTS

In a general embodiment the frame may be constructed from lightweight but durable metal and may be height-adjustable to work with surgeons of varying statures and operating table configurations, and sitting or standing positions. The base of the frame ensures stability during use.

The elasticated suspension system may consist of one or more elasticated (polymer or synthetic rubber) band(s) or cord(s) or metal spring(s) securely attached between the frame and the endoscope/camera assembly. This design dynamically offsets the weight of the equipment, allowing the surgeon to move the endoscope freely while minimizing the exertion required to hold the apparatus in position.

A metal spring has the advantage of simple heat sterilization. A polymer band has the advantage of being cheap and light-weight.

A locking attachment device, for example a screw-gate carabiner, secures the endoscope to the elastic suspension element via an attachment point (such as an eye-bolt or hook) on the endoscope, and either via another attachment point on the elastic suspension element or simply by looping the elastic suspension element through an attachment point on the frame.

One or more moveable joints may be present in the frame at one or more locations. This moveable joint may be moveable and reversibly fixable with the use of friction fastenings such as clamps and screws that can easily be adjusted. Or it may be weighted and sprung in the same way as an angle-poise lamp is weighted and sprung. The joint may be a universal joint, such as a ball-and-socket-joint, moveable in several planes (x, y and z) or it may be a 2-dimensional joint moveable in a single plane. The moveable joint may be located, for example, in the bass part of the frame, for example connecting the base and the upright member. Or in another embodiment it may be located between the upright member and the lateral support beam. Other positions and orientations are anticipated by the invention.

In one embodiment an elongated flexible tie is attached to the distal end of the lateral support beam. The elongated flexible tie itself has a proximal end and a distal end to which is attached, and from which is suspended, the endoscope (or other surgical equipment). The elongated flexible tie comprises a polymer or a spring portion that has flexible and elastic properties, and is adapted to hold the weight of the suspended endoscope and camera apparatus.

Elasticity is typically measured using Young's modulus (E), which quantifies a material's stiffness. The units are: Pascals (Pa) in SI units (1 Pa=1 N/m$^2$), often expressed in megapascals (MPa) or gigapascals (GPa) for common materials. An exercise band is highly elastic and behaves like a rubber-like polymer. Its Young's modulus depends on the material (usually latex or synthetic rubber) and varies widely: Latex resistance bands: Typically 1-10 MPa (with 1 being stretchier than 10 MPa). Synthetic rubber bands: Can be higher, depending on the composition. Stretch ratio: Can extend 200-600% of its original length before significant resistance builds. The non-elasticated portion may have a Young's modulus (E) of, for example 2-100 GPa and be made of various materials such as Nylon Rope: 2-4 GPa, Polyester Rope: 3-4 GPa, Polypropylene Rope: 1.5-2 GPa, Kevlar Rope: 60-130 GPa, or Steel Wire Rope: c. 200 GPa.

The present elasticated portion of the elongated flexible tie or metal spring may be may have a Young's modulus (E) of, for example, from 0.5-100 MPa, or 1.0-50 MPa.

The elongated flexible tie may optionally comprise an elastic portion and a non-elastic portion composed of a wire, or chain, or polymer or any other suitable substance. In certain embodiments there may be one or more elasticated portions and one or more non-elasticated portions.

The tension in the elastic portion may, in some embodiments, be adjusted. Controlled adjustment of tension may be made by various means, for example and adjustable frame mounting may be used where the top end of the band is secured to a movable clamp or sliding bracket on the frame. The bracket can be raised or lowered using a rack-and-pinion mechanism, a lead screw, or a motorized actuator to increase or decrease the stretch in the band.

Alternatively a rotatable spool or winch may be used wherein the top end of the band is wound around a small spool or winch, mounted on the frame. Turning the spool (manually or via a servo motor) winds or unwinds the band, altering its effective length and thus adjusting tension.

Alternatively a spring-loaded tensioner could be used which can be attached at the top or bottom end of the band to dynamically adjust tension. A set screw or locking pin can be used to set a specific tension level.

Or alternatively a pneumatic or hydraulic adjuster could be used comprising a fluid-filled chamber near the attachment point that can be expanded or contracted to vary the tension applied to the band. This allows for fine-tuned tension adjustments based on user requirements.

The invention disclosed herein solves the problem of muscle fatigue when performing endoscopic surgery. It also has the advantage of being a passive solution, and can be made compact to support smaller instruments. Also, multiple instruments may be supported by the same system using multiple elongated flexible ties. Other embodiments use Hybrid mechanical-electronic solutions for precise real-time adjustments. The invention also provides and affordable dynamic balancing systems where budget is a consideration (as it often is).

The preferred embodiment disclosed herein to suspend an endoscope while in use by a surgeon basically used an elasticated cord selected to have an appropriate length and Young's modulus. But there are other systems that may be used with the present invention that can provide a dynamic (i.e. changeable/adaptable) balanced support system that automatically compensate for weight variations of suspended tools or instruments. Such a system may be called a dynamic force adjustment mechanism. These systems are designed to maintain equilibrium dynamically as weight is added or removed. Some well-known mechanisms include the following.

Spring-Balanced Tool Balancers can be used to suspend an endoscope. They incorporate a constant-force spring that automatically adjusts to varying tool weights. This is similar to a retractable spring balancer used in assembly lines.

Pneumatic or Gas Spring Systems could be used. These utilize compressed air or gas springs to counterbalance weight. They can dynamically adjust to different loads.

Counterweight Systems can traditionally be used with mechanical counterweights that move in response to added/removed weight. Such systems are common for use with camera rigs.

Active Force Compensation Systems may also be used. These use sensors and motors to dynamically adjust tension and maintain balance.

Another embodiment may use a power-operated gimbal similar to those used in professional cinematography, providing automated stabilization and further precision control.

A further embodiment may employ a spring-based equilibrium system, akin to an angle-poise lamp, offering an alternative passive counterbalance mechanism.

The elongated flexible tie may be attached at its proximal (upper) end to the lateral support beam by any suitable means (fixture) such as a detachable clip or carabiner ("a modular attachment interface").

Preferably the fixture allows simple attachment and detachment of the elongated flexible tie to/from the lateral support beam. In a preferred embodiment a screw-gate carabiner is used and a ring or eye or similar attachment point is provided both on the distal end of the lateral support beam and the proximal end of the elongated flexible tie.

Figure 2:
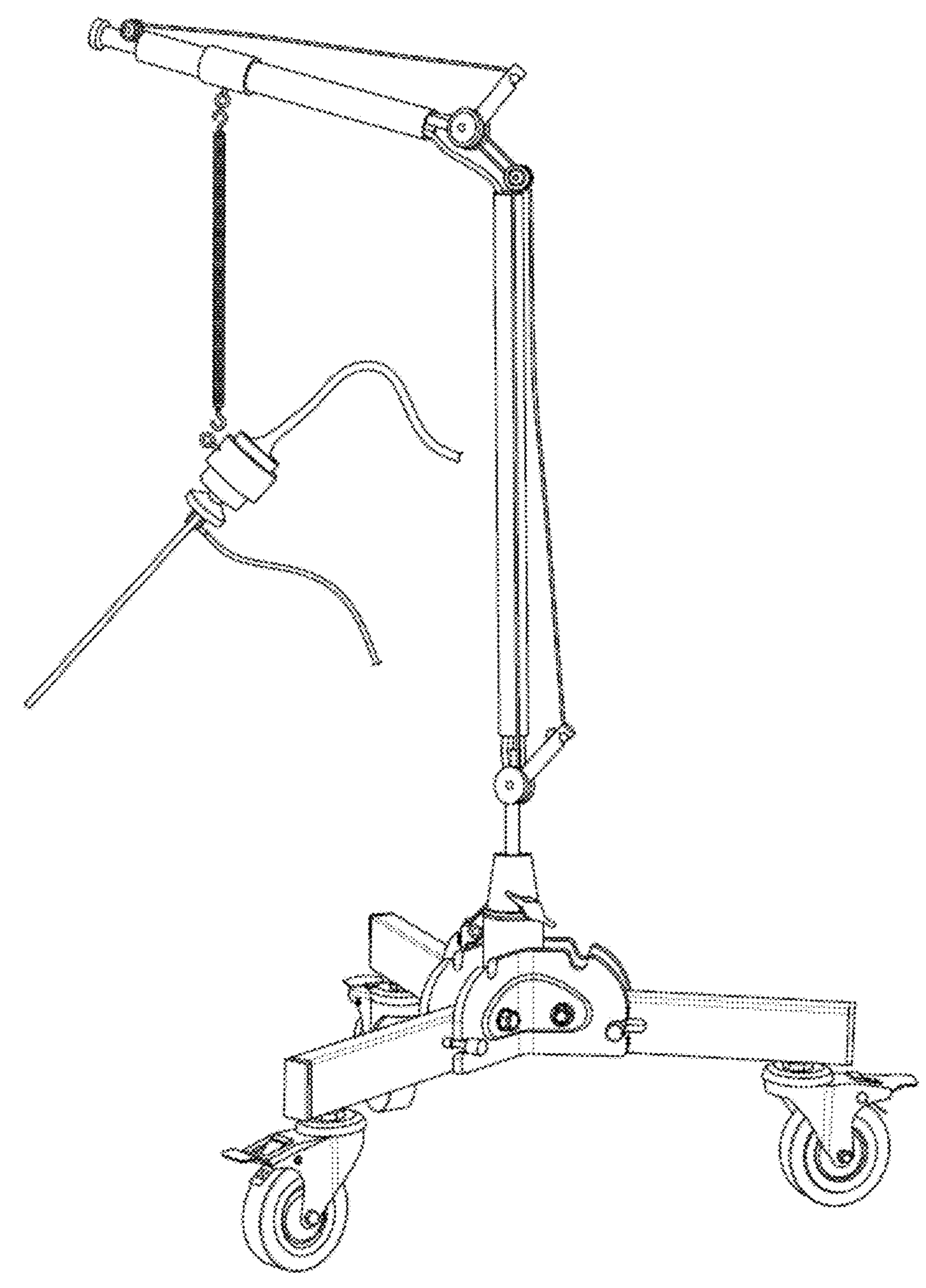
FIG. 2: Perspective view of the elasticated suspension system and frame of the invention further comprising an "angle-poise" type a dynamic force adjustment mechanism using constant-force springs
Figure 3:
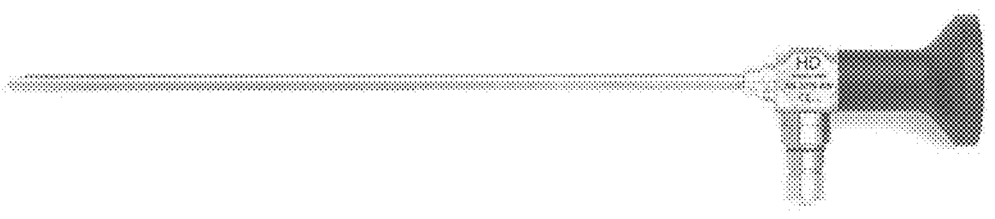
FIG. 3: Shows a typical ridged ENT endoscope for use with the invention.
Figure 4:
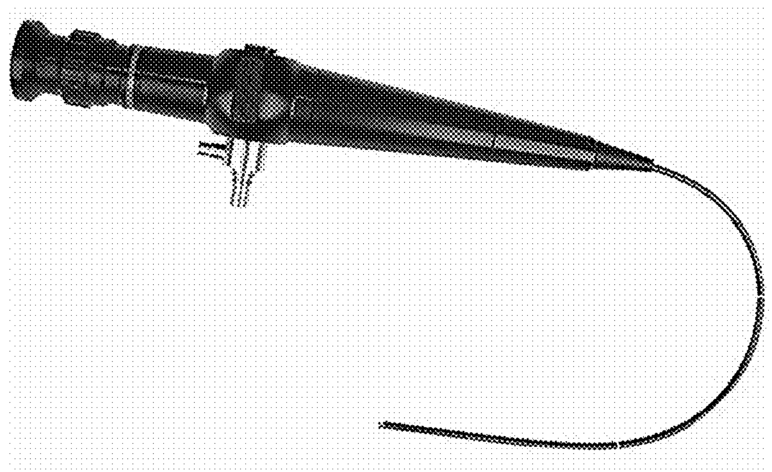
FIG. 4: Shows a typical flexible ENT endoscope for use with the invention.

FIGS. 1 and 2 show an endoscope with an eye bolt that allows attachment of the elongated flexible tie. But not all endoscopes (specifically ENT endoscopes) have suitable attachment points (see FIGS. 3 and 4). It is of critical practical importance to be able to connect the distal end of the elongated flexible tie to the endoscope, such that the connection is (1) secure, and (2) attaches at a point approximately near the mid balance point (the centre of mass or centre of gravity) of the endoscope, so that approximately half the weight of the endoscope/camera device is distributed on either side of the attachment point. Preferably the connector should connect at a connection point whereby the weight distribution should be no more than 60:40 either side of the balance point or the connection point. More preferably no more than 55:45.

To provide this the present invention includes a harness adapted to fit onto most versions of commercially available endoscopes. The harness is adapted to easily and removably fit onto an endoscope and also to be sterilisable by heat sterilization. In another embodiment the harness is disposable. The harness may be made of any material that can be heat-sterilized such as Nylon (polyamide, heat-stabilized grades).

By incorporating multiple embodiments, the invention extends its applicability across different surgical techniques, broadening commercial potential and reducing the likelihood of design workarounds.

Methods for Using the Device of the Invention

When in use, the surgeon will generally be resting his hand on the endoscope such that the elasticated element resists the combined force of the weight of the endoscope and the hand/arm of the surgeon. Thus the elastic force is set and adapted to resist that combined force. The invention may provide a selection of elastic elements to suit the surgeon. Alternatively it may comprise a dynamic force adjustment mechanism as described herein.

In use, a patient will be resting an adjustable table or seat and the surgeon will be sitting on a seat adjacent to the patient. The endoscope and camera are weighed (or the weight is known and noted). A suitable elastic setting is selected depending on and calculated in proportion to the weight of the endoscope and camera (we shall just refer to this combination as the endoscope). This means that an appropriate elastic elongated flexible tie is selected. Or in another embodiment, the dynamic force adjustment mechanism is adjusted to support a suitable weight range. The frame of the device of the invention is positioned securely in place to the side of the patient such that the the elongated flexible tie dangles down from the lateral support beam to a desirable height. The endoscope is then attached via a locking carabiner. Further fine adjustments may be made to the height and tension of the system to provide an ideal position and support for the endoscope. The surgeon may then use the endoscope as usual, except that little muscular support is required and when not in use the endoscope may be left suspended without a need to rest it on a surface.

The invention claimed is:

1. A dynamic suspension system for supporting an endoscope and camera combination during functional endoscopic sinus surgery, comprising:

(i) a stable base adapted to rest on a floor;

(ii) an upright support frame extending from the base, having a proximal end attached to the base, and a distal end; and (iii) a lateral support beam having a proximal end attached to the distal end of the upright support frame; and a distal end to which is attached (iv) an interchangeable elasticated polymer or synthetic rubber band which has a Young's modulus of 1-10 MPa, hanging vertically therefrom;

wherein the elasticated polymer or synthetic rubber band provides controlled resistance and counterbalances the weight of the endoscope, allowing dynamic movement with minimal force;

wherein the interchangeable elasticated polymer or synthetic rubber band is connected at a lower end to (v) an endoscope/camera assembly;

wherein the interchangeable elasticated polymer or synthetic rubber band is connected to the endoscope/camera assembly by a connector, wherein the connector is attached at a point approximately at the mid balance point of the endoscope/camera assembly;

wherein the interchangeable elasticated polymer band elasticated polymer or synthetic rubber band provides controlled resistance and counterbalances the weight of the endoscope, allowing dynamic movement with minimal force wherein the endoscope comprises a rigid nasal endoscope having a weight in a range of 200 to 400 grams;

wherein the interchangeable elasticated polymer or synthetic rubber band is selected to have a length and Young's modulus that counterbalance the weight of the rigid nasal endoscope so that the endoscope/camera assembly is supported in a free-floating condition over a working range of motion during functional endoscopic sinus surgery;

wherein the free-floating condition allows the endoscope/camera assembly to be continuously repositioned by a surgeon using low-force single-hand input without requiring a rigid metal holder to lock the endoscope/camera assembly in a fixed operative position during repositioning; and wherein the free-floating condition reduces sustained muscular load on the surgeon while permitting continuous fine adjustment of the endoscope/camera assembly during functional endoscopic sinus surgery.

2. The system of claim 1, wherein the elasticated polymer band is a synthetic rubber tube configured to exhibit non-linear elastic elongation characteristics such that counterbalancing force remains substantially constant over said working range of vertical displacement.

3. A method for supporting an endoscope and camera assembly using a dynamic suspension system during endoscopic sinus surgery, comprising:

(A) providing a dynamic suspension system for supporting an endoscope and camera combination during functional endoscopic sinus surgery, comprising:

(i) a stable base adapted to rest on a floor;

(ii) an upright support frame extending from the base, having a proximal end attached to the base, and a distal end; and (iii) a lateral support beam having a proximal end attached to the distal end of the upright support frame; and a distal end to which is attached (iv) an interchangeable elasticated polymer or synthetic rubber band which has a Young's modulus of 1-10 MPa, hanging vertically therefrom;

wherein the elasticated polymer or synthetic rubber band provides controlled resistance and counterbalances the weight of the endoscope, allowing dynamic movement with minimal force;

wherein the interchangeable elasticated polymer or synthetic rubber band is connected at a lower end to (v) an endoscope/camera assembly;

wherein the interchangeable elasticated polymer or synthetic rubber band is connected to the endoscope/camera assembly by a connector, wherein the connector is attached at a point approximately at the mid balance point of the endoscope/camera assembly;

wherein the elasticated polymer or synthetic rubber band maintains the endoscope/camera assembly in a neutrally balanced, free-floating condition during use;

(B) positioning the stable base on a surgical floor or table; adjusting an upright support frame to a suitable height; securing the endoscope/camera assembly to the interchangeable elasticated polymer or synthetic rubber band and continuously repositioning the endoscope/camera assembly during surgery using low-force manual input without engaging any locking mechanism to dynamically support and reposition the endoscope with minimal muscular effort.

4. The method of claim 3, further comprising modifying the elasticity of the elasticated polymer or synthetic rubber band by selecting an elasticated polymer or synthetic rubber band elastic component with a desired Young's modulus such that the dynamic suspension system is tuned to maintain said neutrally balanced, free-floating condition for a selected endoscope weight range.

* * * * *